United States Patent
Jones et al.

(10) Patent No.: US 6,521,865 B1
(45) Date of Patent: Feb. 18, 2003

(54) PULSED FIBER LASER CUTTING SYSTEM FOR MEDICAL IMPLANTS

(75) Inventors: Stephen Jones, Saugus, CA (US); Klaus Kleine, Los Gatos, CA (US); Brad Whitney, Oakland, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 60 days.

(21) Appl. No.: 09/882,590

(22) Filed: Jun. 14, 2001

(51) Int. Cl.$^7$ .............................................. B23K 26/38
(52) U.S. Cl. .................................................. 219/121.72
(58) Field of Search ........................ 219/121.6, 121.67, 219/121.68, 121.69, 121.7, 121.71, 121.72, 121.85

(56) References Cited

U.S. PATENT DOCUMENTS

| | | |
|---|---|---|
| 4,387,952 A | 6/1983 | Slusher |
| 4,733,665 A | 3/1988 | Palmaz |
| 4,963,022 A | 10/1990 | Sommargren |
| 4,994,071 A | 2/1991 | MacGregor |
| 5,073,694 A | 12/1991 | Tessier et al. |
| 5,102,417 A | 4/1992 | Palmaz |
| 5,345,057 A | 9/1994 | Muller |
| 5,514,154 A | 5/1996 | Lau et al. |
| 5,569,295 A | 10/1996 | Lam |
| 5,591,197 A | 1/1997 | Orth et al. |
| 5,759,192 A | 6/1998 | Saunders |
| 6,160,240 A * | 12/2000 | Momma et al. ........ 219/121.85 |
| 6,287,336 B1 * | 9/2001 | Globerman et al. |

FOREIGN PATENT DOCUMENTS

| | | |
|---|---|---|
| EP | 0 221 570 A2 | 5/1987 |
| EP | 0 364 787 A1 | 4/1990 |
| EP | 0 372 789 A3 | 6/1990 |
| EP | 0 421 729 A2 | 4/1991 |
| EP | 0 540 290 A2 | 5/1993 |
| EP | 0 541 443 A1 | 5/1993 |
| EP | 0 562 150 A1 | 9/1993 |
| EP | 0 624 421 A2 | 11/1994 |
| EP | 0 662 307 A1 | 7/1995 |
| EP | 0 679 373 A2 | 11/1995 |
| GB | 2 070 490 A | 9/1981 |
| WO | WO 92/06734 | 4/1992 |

OTHER PUBLICATIONS

Anorad Corporation, *Anomatic*™ *Positioning Controller* (undated) Brochure.

* cited by examiner

*Primary Examiner*—Samuel M. Heinrich

(57) ABSTRACT

An improved expandable stent for implantation in a body lumen, such as an artery, and an improved method for making it from a single length of tubing. The stent consists of a plurality of radially expandable cut cylindrical elements generally aligned on a common axis and interconnected by one or more interconnective elements, the elements having a rectangular cross-section from cut-to-cut. The individual radially expandable cylindrical elements are disposed in an undulating pattern. The stent is manufactured by direct laser cutting from a single metal tube using a finely focused laser beam originating from a diode pumped fiber laser with an external pulse generator and passing through a coaxial gas jet structure to impinge on the working surface of the tube as the linear and rotary velocity of the tube is precisely controlled.

13 Claims, 5 Drawing Sheets

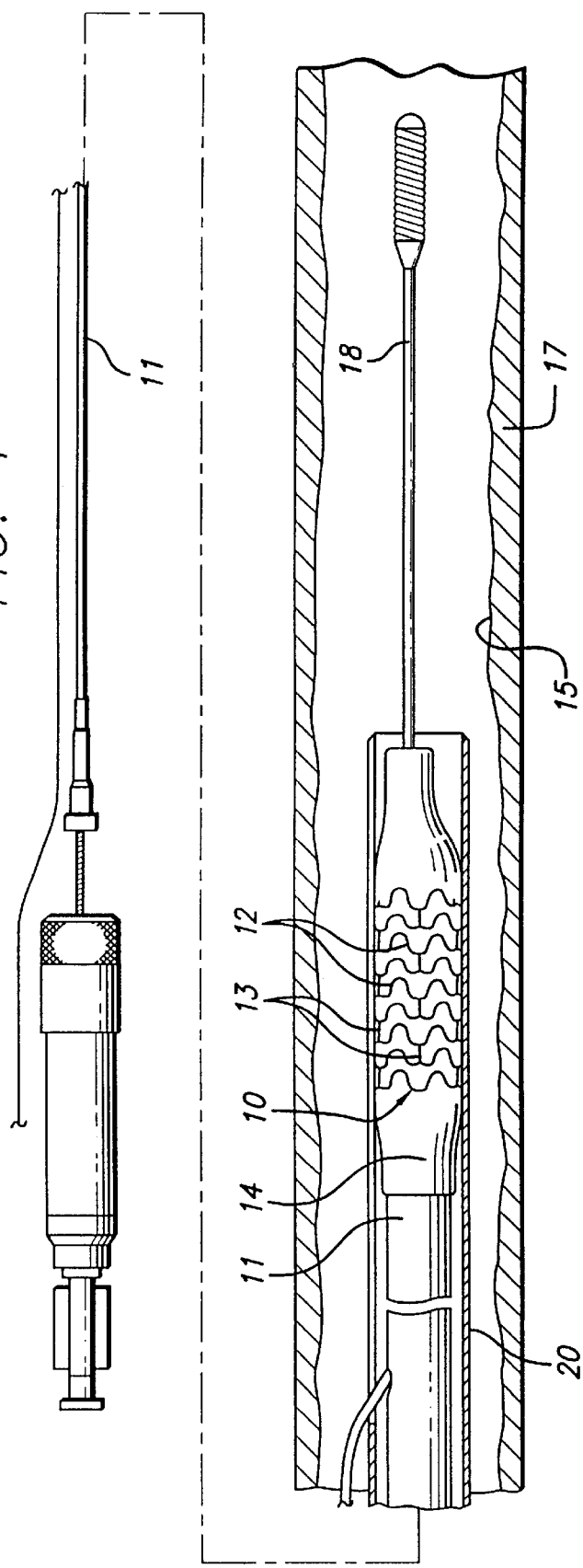
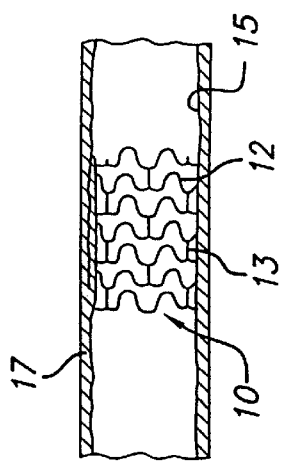
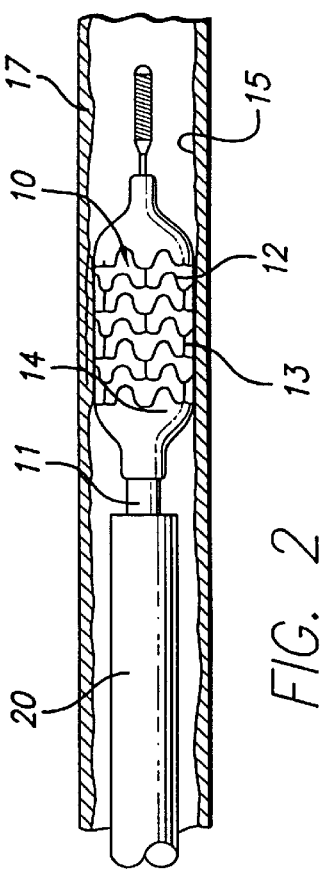

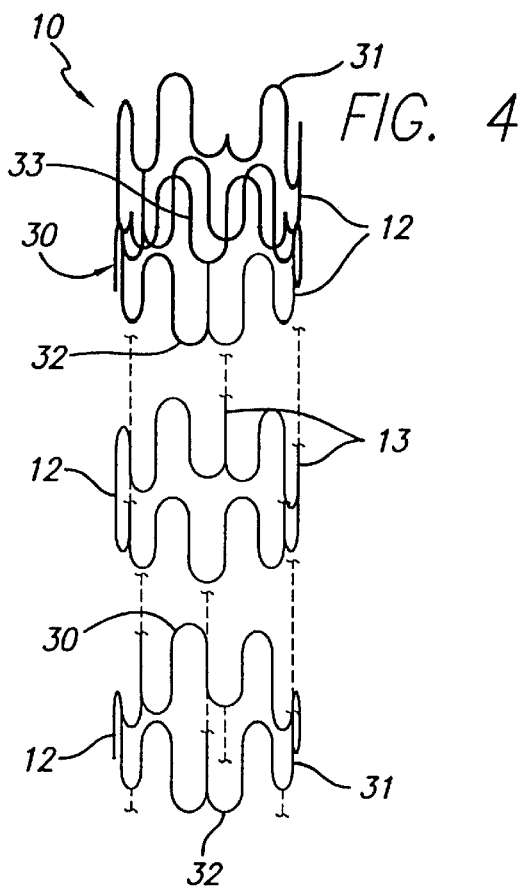
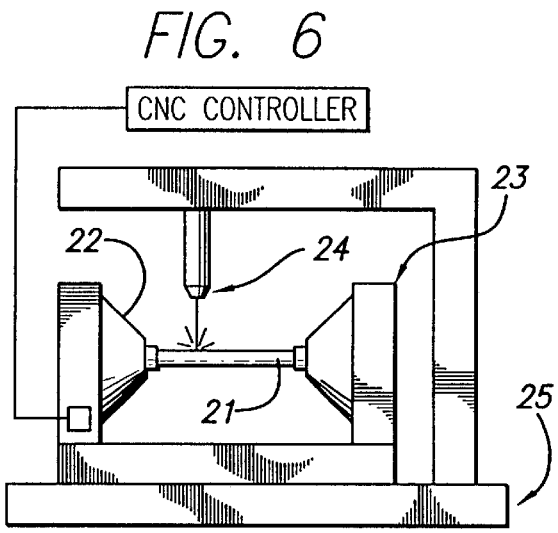
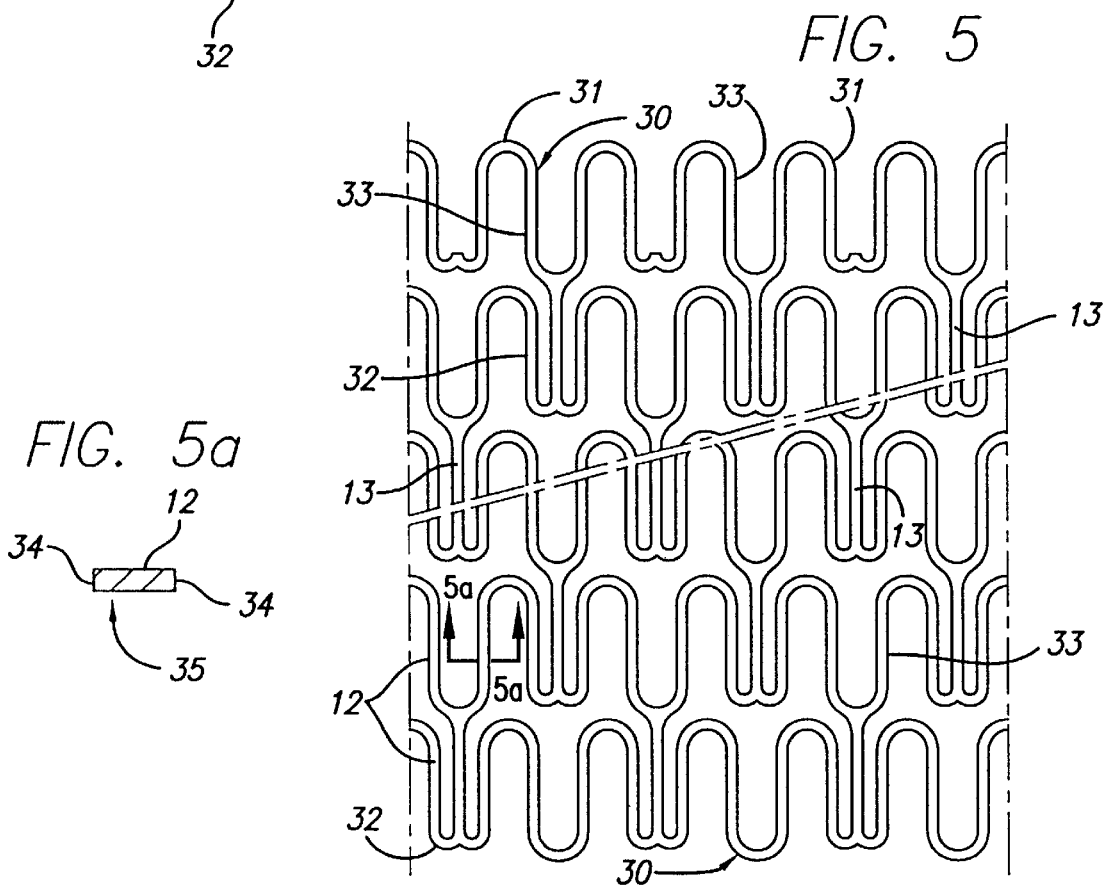

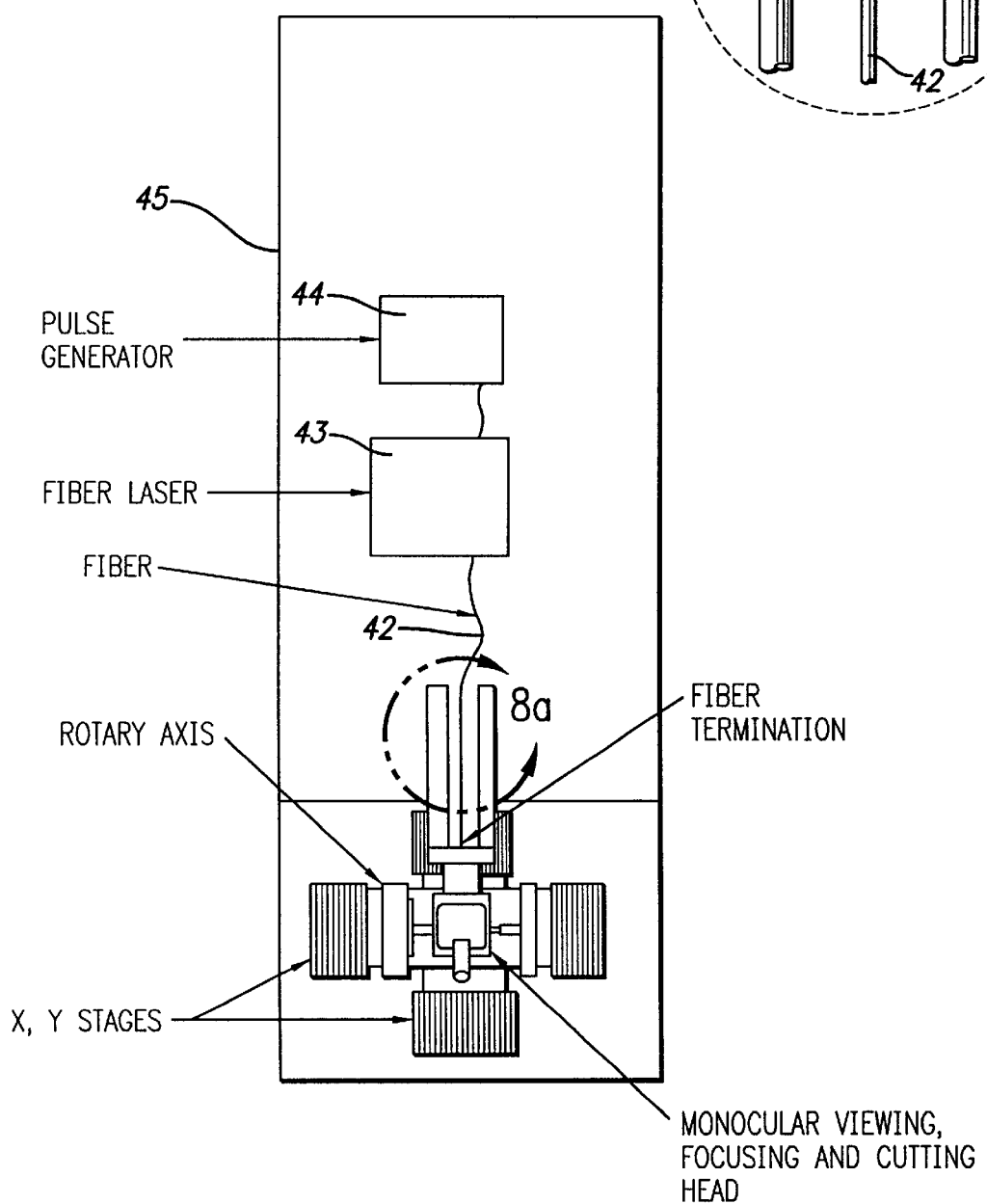

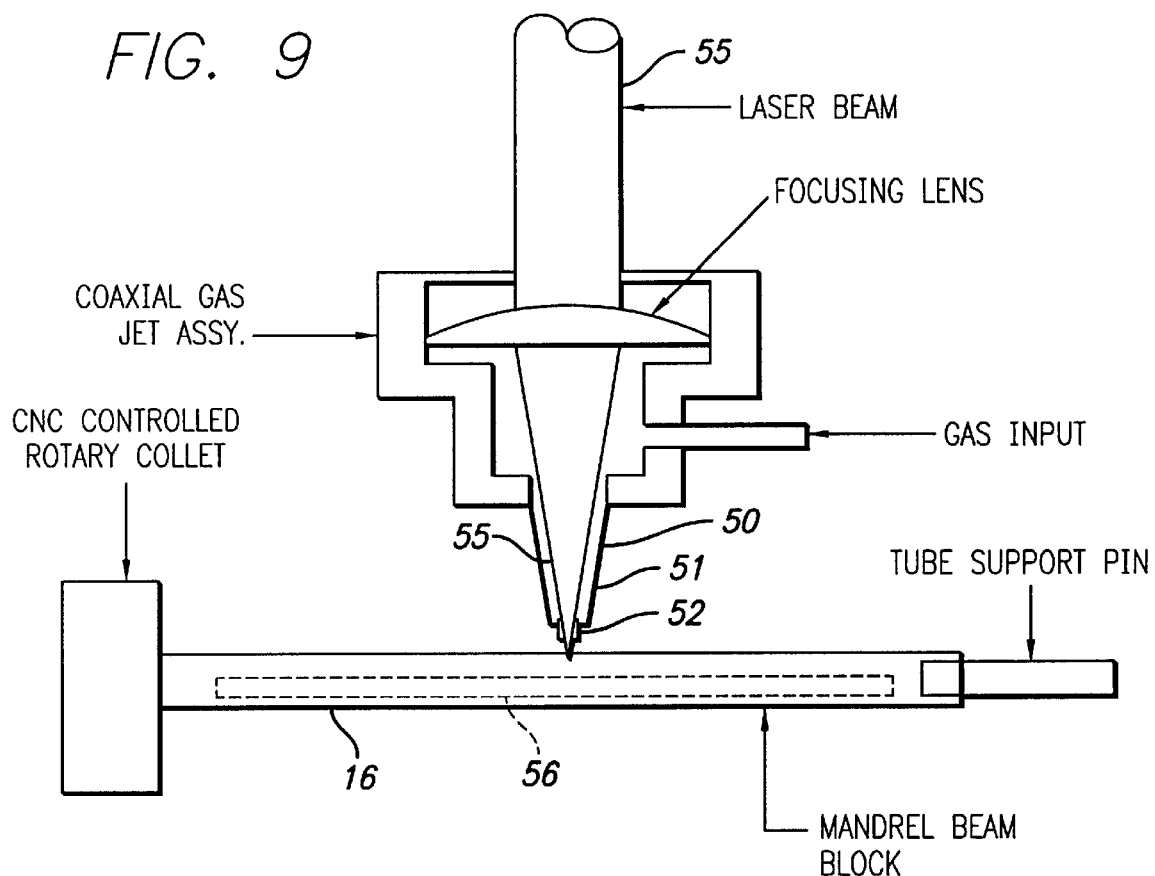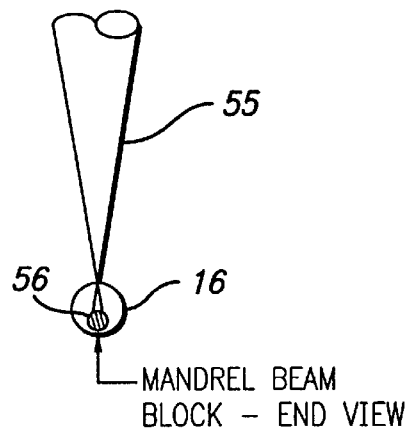

PULSED FIBER LASER CUTTING SYSTEM FOR MEDICAL IMPLANTS

BACKGROUND OF THE INVENTION

This invention relates generally to improvements in the manufacture of expandable metal stents and, more particularly, to new and improved methods and apparatus for direct laser cutting of metal stents and providing stents of enhanced structural quality.

Stents are expandable endoprosthesis devices which are adapted to be implanted into a patient's body lumen, such as a blood vessel, to maintain the patency of the vessel. These devices are typically used in the treatment of atherosclerotic stenosis in blood vessels and the like.

In the medical arts, stents are generally tubular-shaped devices which function to hold open a segment of a blood vessel or other anatomical lumen. They are particularly suitable for use to support and hold back a dissected arterial lining which can occlude the fluid passageway.

Various means have been provided to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter.

One example of a particularly useful expandable stent is a stent which is relatively flexible along its longitudinal axis to facilitate delivery through tortuous body lumens, but which is stiff and stable enough radially in an expanded condition to maintain the patency of a body lumen such as an artery when implanted within the lumen. Such a desirable stent typically includes a plurality of radially expandable cylindrical elements which are relatively independent in their ability to expand and to flex relative to one another. The individual radially expandable cylindrical elements of the stent are precisely dimensioned so as to be longitudinally shorter than their own diameters. Interconnecting elements or struts extending between adjacent cylindrical elements provide increased stability and are positioned to prevent warping of the stent when it is expanded. The resulting stent structure is a series of radially expandable cylindrical elements which are spaced longitudinally close enough so that small dissections in the wall of a body lumen may be pressed back into position against the lumenal wall, but not so close as to compromise the longitudinal flexibility of the stent. The individual cylindrical elements may rotate slightly relative to adjacent cylindrical elements without significant deformation, cumulatively giving a stent which is flexible along its length and about its longitudinal axis, but is still very stiff in the radial direction in order to resist collapse.

The prior art stents generally have a precisely laid out circumferential undulating pattern, e.g. serpentine. The transverse cross-section of the undulating component of the cylindrical element is relatively small and preferably has an aspect ratio of about two to one to about 0.5 to one. A one-to-one aspect ratio also has been found particularly suitable. The open reticulated structure of the stent allows for the perfusion of blood over a large portion of the arterial wall which can improve the healing and repair of a damaged arterial lining.

The radial expansion of the expandable cylinder deforms the undulating pattern similar to changes in a waveform which result from decreasing the waveform's amplitude and the frequency. In the case of a balloon-expandable stent, such as one made from stainless steel, the cylindrical structures of the stent are plastically deformed when expanded so that the stent will remain in the expanded condition and, therefore, they must be sufficiently rigid when expanded to prevent their collapse in use. During expansion of the stent, portions of the undulating pattern may tip outwardly resulting in projecting members on the outer surface of the expanded stent. These projecting members tip radially outwardly from the outer surface of the stent and embed in the vessel wall and help secure the expanded stent so that it does not move once it is implanted.

The elements or struts which interconnect adjacent cylindrical elements should have a precisely defined transverse cross-section similar to the transverse dimensions of the undulating components of the expandable cylindrical elements. The interconnecting elements may be formed as a unitary structure with the expandable cylindrical elements from the same intermediate product, such as a tubular element, or they may be formed independently and connected by suitable means, such as by welding or by mechanically securing the ends of the interconnecting elements to the ends of the expandable cylindrical elements. Preferably, all of the interconnecting elements of a stent are joined at either the peaks or the valleys of the undulating structure of the cylindrical elements which form the stent. In this manner, there is minimal or no shortening of the stent upon expansion.

The number and location of elements interconnecting adjacent cylindrical elements can be varied in order to develop the desired longitudinal flexibility in the stent structure both in the unexpanded, as well as the expanded condition. These properties are important to minimize alteration of the natural physiology of the body lumen into which the stent is implanted and to maintain the compliance of the body lumen which is internally supported by the stent. Generally, the greater the longitudinal flexibility of the stent, the easier and the more safely it can be delivered to the implantation site.

It will be apparent from the foregoing that conventional stents are very high precision, relatively fragile devices and, ideally, the most desirable metal stents incorporate a fine precision structure cut from a very small diameter, thin-walled cylindrical tube. In this regard, it is extremely important to make precisely dimensioned, smooth, narrow cuts in the stainless tubes in extremely fine geometries without damaging the narrow struts that make up the stent structure. While the various laser cutting processes and chemical etching, heretofore utilized by the prior art to form such expandable metal stents, have been adequate, improvements have been sought to provide stents of enhanced structural quality in terms of resolution, reliability and yield.

Accordingly, those concerned with the development, manufacture and use of metal stents have long recognized the need for improved manufacturing processes for such stents. The present invention fulfills these needs.

SUMMARY OF THE INVENTION

Briefly, and in general terms, the present invention provides a new and improved method and apparatus for direct laser cutting of metal stents enabling greater precision, reliability, structural integrity and overall quality, while minimizing burrs, slag or other imperfections which might otherwise hamper stent integrity and performance.

The present invention provides an improved system for producing metal stents with a fine precision structure cut from a small diameter, thin-walled, cylindrical tube. The tubes are typically made of stainless steel and are fixtured under a laser and positioned utilizing CNC (computer numerical control) to generate a very intricate and precise pattern. Due to the thin-wall and the small geometry of the stent pattern, it is necessary to have very precise control of the laser, its power level, and the precise positioning of the laser cutting path.

In one embodiment of the invention, in order to minimize the heat input, which prevents thermal distortion, uncontrolled burn-out of the metal, and metallurgical damage due to excessive heat, a diode pumped fiber laser is utilized. Further, an external pulse generator is employed so that laser pulses having pulse lengths between 0.05 and 0.50 milliseconds are achieved at a frequency range of 100 to 3000 Hz. With these parameters, it is possible to make smooth, narrow cuts in the stainless steel tubes in very fine geometries without damaging the narrow struts that make up the stent structure.

In addition to the laser and the precision CNC positioning equipment, a coaxial gas jet is also utilized to provide for additional heat reduction in the workpiece by introducing a gas stream that surrounds the focused laser beam and is directed along the beam axis. The coaxial gas jet nozzle is centered around the focused beam with approximately 0.010 inch (0.254 mm) between the tip of the nozzle and the tubing. The jet is pressurized with oxygen at 20 psi and is directed at the tube with the focused laser beam exiting the tip of the nozzle. The oxygen reacts with the metal to assist in the cutting process very similar to oxyacetylene cutting. The focused laser beam acts as an ignition source and controls the reaction of the oxygen with the metal. In this manner, it is possible to cut the material with a very fine kerf with precision. In order to prevent burning by the beam and/or molten slag on the far wall of the tube inside diameter, a stainless steel mandrel is placed inside the tube and is allowed to roll on the bottom of the tube as the pattern is cut. This acts as a beam/debris block protecting the far wall inside diameter.

The cutting process utilizing oxygen with the finely focused diode pumped fiber laser beam results in a very narrow kerf (approximately 0.0005 inch or 0.0127 mm) with the molten slag re-solidifying along the cut. This traps the cut-out scrap of the pattern and requires further processing. In order to remove the slag debris from the cut and allow the scrap to be removed from the remaining stent pattern, it is desirable to soak the cut tube in a solution of HCl for a selected time and temperature. Before it is soaked, the tube is placed in a bath of alcohol/water solution and ultrasonically cleaned for approximately 1 minute to remove the loose debris left from the cutting operation. After soaking, the tube is then ultrasonically cleaned in the heated HCl for a period of time dependent upon the wall thickness. To prevent cracking or breaking of the struts attached to the material left at the two ends of the stent pattern due to harmonic oscillations induced by the ultrasonic cleaner, a mandrel is placed down the center of the tube during the cleaning/scrap removal process. Upon completion of this process, the stent structures are rinsed in water and are then ready for electropolishing.

Hence, the new and improved method and apparatus for direct laser cutting of metal stents, in accordance with the present invention, makes accurate, reliable, high resolution, expandable stents with patterns having smooth, narrow cuts and very fine geometries.

The above and other objects and advantages of this invention will be apparent from the following more detailed description when taken in conjunction with the accompanying drawings of exemplary embodiments.

BRIEF DESCRIPTION OF THE DRAWINGS

FIG. 1 is an elevational view, partially in section, of a stent embodying features of the invention which is mounted on a delivery catheter and disposed within an artery.

FIG. 2 is an elevational view, partially in section, similar to that shown in FIG. 1, wherein the stent is expanded within an artery.

FIG. 3 is an elevational view, partially in section, showing the expanded stent within the artery after withdrawal of the delivery catheter.

FIG. 4 is a perspective view of a stent embodiment in an unexpanded state, with one end of the stent being shown in an exploded view to illustrate the details thereof.

FIG. 5 is a plan view of a flattened section of a stent of the invention which illustrates the undulating pattern of the stent as shown in FIG. 4.

FIG. 5a is a sectional view taken along the line 5a—5a in FIG. 5.

FIG. 6 is a schematic representation of equipment for selectively cutting the tubing in the manufacture of stents, in accordance with the present invention.

FIG. 8 is a plan view of the laser head and optical delivery subsystem for the laser cutting system shown in FIG. 7.

FIG. 8a is a partial enlarged view depicting the parallel mirrors.

FIG. 9 is an elevational view of a coaxial gas jet, rotary collect, tube support and beam blocking apparatus for use in the laser cutting system shown in FIG. 7.

FIG. 10 is a sectional view taken along the line 10—10 in FIG. 9.

DETAILED DESCRIPTION OF THE PREFERRED EMBODIMENTS

Figure 7:
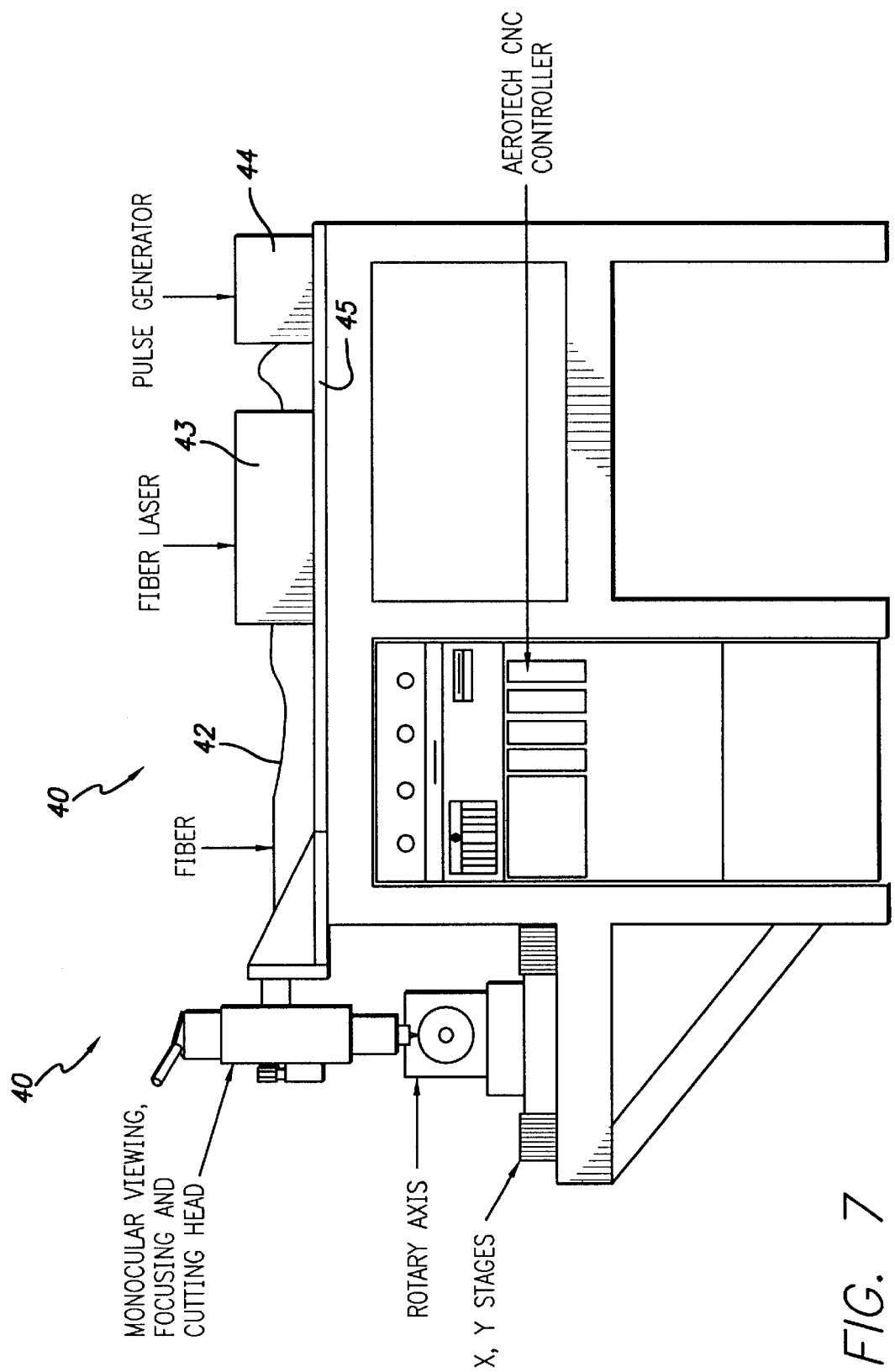
FIG. 7 is an elevational view of a system for cutting an appropriate pattern by laser in a metal tube to form a stent, in accordance with the present invention.

Referring now to the drawings, and particularly FIG. 1, there is shown a stent 10 that is mounted onto a delivery catheter 11. The stent is a high precision patterned tubular device. The stent typically comprises a plurality of radially expanded cylindrical elements 12 disposed generally coaxially and interconnected by elements 13 disposed between adjacent cylindrical elements. The delivery catheter has an expandable portion or balloon 14 for expanding of the stent within an artery 15.

The typical delivery catheter 11 onto which the stent 10 is mounted is essentially the same as a conventional balloon dilatation catheter for angioplasty procedures. The balloon 14 may be formed of suitable materials such as polyethylene, polyethylene terephthalate, polyvinyl chloride, nylon and ionomers such as Surlyn® manufactured by the Polymer Products Division of the Du Pont Company. Other polymers may also be used. In order for the stent to remain in place on the balloon during delivery to the site of the damage within the artery 15, the stent is compressed onto the balloon. A retractable protective delivery sheath 20 may be provided to further ensure that the stent stays in place on the expandable portion of the delivery catheter and prevent abrasion of the body lumen by the open surface of the stent during delivery to the desired arterial location. Other means for securing the stent onto the balloon may also be used, such as providing collars or ridges on the ends of the working portion, i.e., the cylindrical portion, of the balloon.

The delivery of the stent 10 is accomplished in the following manner. The stent is first mounted onto the inflatable balloon 14 on the distal extremity of the delivery catheter 11. The balloon is slightly inflated to secure the stent onto the exterior of the balloon. The catheter-stent assembly is introduced within the patient's vasculature in a conventional Seldinger technique through a guiding catheter (not shown). A guidewire 18 is disposed across the target arterial section and then the catheter/stent assembly is advanced over the guidewire within the artery 15 until the stent is positioned in the target area. The balloon of the catheter is expanded, expanding the stent against the artery, which is illustrated in FIG. 2. While not shown in the drawing, the artery is preferably expanded slightly by the expansion of the stent to seat or otherwise fix the stent to prevent movement. In some circumstances during the treatment of stenotic portions of an artery, the artery may have to be expanded considerably in order to facilitate passage of blood or other fluid therethrough.

The stent 10 serves to hold open the artery 15 after the catheter 11 is withdrawn, as illustrated by FIG. 3. Due to the formation of the stent from an elongated tubular member, the undulating component of the cylindrical elements of the stent is relatively flat in transverse cross-section, so that when the stent is expanded, the cylindrical elements are pressed into the wall of the artery and, as a result, do not interfere with the blood flow through the artery. The cylindrical elements 12 of the stent, which are pressed into the wall of the artery, will eventually be covered with endothelial cell growth which further minimizes blood flow interference. The undulating portion of the cylindrical elements provides good tacking characteristics to prevent stent movement within the artery. Furthermore, the closely spaced cylindrical elements at regular intervals provide uniform support for the wall of the artery and, consequently, are well adapted to tack up and hold in place small flaps or dissections in the wall of the artery.

FIG. 4 is an enlarged perspective view of the stent 10 shown in FIG. 1 with one end of the stent shown in an exploded view to illustrate in greater detail the placement of interconnecting elements 13 between adjacent radially expandable cylindrical elements 12. Each pair of interconnecting elements on one side of a cylindrical element are preferably placed to allow maximum flexibility for a stent. In the embodiment shown in FIG. 4, the stent has three interconnecting elements between adjacent radially expandable cylindrical elements that are 120° apart. Each pair of interconnecting elements on one side of a cylindrical element are offset radially 60° from the pair on the other side of the cylindrical element. The alternation of the interconnecting elements results in a stent which is longitudinally flexible in essentially all directions. The primary flexibility of this stent design derives from the cylindrical elements, while the interconnecting element actually reduces the overall stent flexibility. Various configurations for the placement of interconnecting elements are possible. However, as previously mentioned, all of the interconnecting elements of an individual stent should be secured to either the peaks or valleys of the undulating structural elements in order to prevent shortening of the stent during the expansion thereof.

The number of undulations may also be varied to accommodate placement of interconnecting elements 13, e.g., at the peaks of the undulations or along the sides of the undulations as shown in FIG. 5.

As best observed in FIGS. 4 and 5, the cylindrical elements 12 are in the form of a serpentine pattern 30. As previously mentioned, each cylindrical element is connected by interconnecting elements 13. The serpentine pattern is made up of a plurality of U-shaped members 31, W-shaped members 32, and Y-shaped members 33, each having a different radius so that expansion forces are more evenly distributed over the various members.

The aforedescribed illustrative stent 10 and similar stent structures can be made in many ways. However, the preferred method of making the stent is to cut a thin-walled tubular member 16, such as stainless steel tubing, to remove portions of the tubing in the desired pattern for the stent, leaving relatively untouched the portions of the metallic tubing which are to form the stent.

The tubing 16 may be made of a suitable biocompatible material such as stainless steel. For example, the stainless steel tubing may be Alloy type 316L SS, Special Chemistry per ASTM F138-92 or ASTM F139-92 grade 2. Special Chemistry of type 316L per ASTM F138-92 or ASTM F139-92 Stainless Steel for surgical implants in weight percent is as follows:

| | |
|---|---|
| Carbon (C) | 0.03% max. |
| Manganese (Mn) | 2.00% max. |
| Phosphorous (P) | 0.025% max. |
| Sulphur (S) | 0.010% max. |
| Silicon (Si) | 0.75% max. |
| Chromium (Cr) | 17.00–19.00% |
| Nickel (Ni) | 13.00–15.50% |
| Molybdenum (Mo) | 2.00–3.00% |
| Nitrogen (N) | 0.10% max. |
| Copper (Cu) | 0.50% max. |
| Iron (Fe) | Balance |

The present invention pulsed fiber laser cutting system can be used to cut any stent pattern and virtually any stent material. The invention is not limited to cutting tubular members made from stainless steel. For example, tubular members being formed from any number of metals are possible, including cobalt-chromium, titanium, nickel-titanium, tantalum, gold, platinum, nickel-titanium-platinum, and other similar metal alloys.

The stent diameter is very small, so the tubing from which it is made must necessarily also have a small diameter. For coronary applications, typically, the stent has an outer diameter on the order of about 0.06 inch (1.524 mm)in the unexpanded condition, equivalent to the tubing from which the stent is made, and can be expanded to an outer diameter of 0.1 inch (2.54 mm) or more. The wall thickness of the tubing is about 0.003 inch (0.0762 mm).

In accordance with the present invention, it is preferred to cut the tubing 16 in the desired pattern by means of a machine-controlled laser as illustrated schematically in FIG. 6. A machine-controlled laser cutting system is generally depicted as disclosed in U.S. Pat. No. 5,780,807 to Richard J. Saunders and is incorporated herein by reference. The tubing 21 is placed in a rotatable collect fixture 22 of a machine-controlled apparatus 23 for positioning the tubing relative to the laser 24. According to machine-encoded instructions, the tubing is rotated and moved longitudinally relative to the laser, which is also machine-controlled. The laser selectively removes the material from the tubing by ablation and a pattern is cut into the tube. The tube is therefore cut into the discrete pattern of the finished stent.

The process of cutting a pattern for the stent into the tubing 16 is automated except for loading and unloading the length of tubing. Referring again to FIG. 6, the cutting may be done, for example, using a CNC-opposing collect fixture 22 for axial rotation of the length of tubing, in conjunction with a CNC X/Y table 25 for movement of the length of tubing axially relative to the machine-controlled laser, as described. The program for control of the apparatus is dependent on the particular configuration used and the pattern to be ablated in the tubing.

Referring now to FIGS. 7–10, there is shown a process and apparatus, in accordance with the present invention, for producing metal stents with a fine precision structure cut from a small diameter thin-walled cylindrical tube 16. Cutting a fine structure (0.0035 inch web width (0.889 mm)) requires precise laser focusing and minimal heat input. In order to satisfy these requirements, an improved laser technology has been adapted to this micro-machining application according to the present invention.

The diode pumped fiber laser 40, as illustrated in FIG. 7, is comprised of an optical fiber 42 and a diode pump 43 integrally mounted coaxial to the optical fiber. In one embodiment, as shown in FIG. 8a, two mirrors 46,47 are mounted within the optical fiber such that the mirrors are parallel to one another and normal to the central axis of the optical fiber. The two mirrors are spaced apart by a fixed distance creating an area within the optical fiber between the mirrors called the active region. This type of fiber laser is typically available from SDL and is rated at 23 watts.

A pulse generator 44 is mounted external to the diode pumped fiber laser 40 in the area of the horizontal mounting surface 45. The pulse generator provides restricted and more precise control of the laser's output by gating the diode pump 43. By employing the external pulse generator, laser pulses having pulse lengths between 0.05 and 0.50 milliseconds are achieved at a frequency range of 100 to 3000 Hz. The pulse generator is a conventional model obtainable from any number of manufacturers and operates on standard 110 volt AC.

The diode pumped fiber laser 40 operates with low-frequency, pulsed wavelengths in order to minimize the heat input into the stent structure, which prevents thermal distortion, uncontrolled burn out of the metal, and metallurgical damage due to excessive heat, and thereby produce a smooth, debris-free cut. In use, the diode pump 43 generates light energy at the proximal end of the optical fiber. Initially, the light energy is pulsed by the external pulse generator 44. Next, the pulsed light energy transmissions pass along the optical fiber 42 and through the first mirror. Between the first and second mirror the light is resonated in the fiber laser's active region. Then, the light passes through the second mirror and continues along the length of the optical fiber. Finally, the light exits the distal end of the fiber and ultimately impinges upon the workpiece.

It will be appreciated by those skilled in the art that, in use, the diode pumped fiber laser 40 of the present invention is low in maintenance because it does not require a flash lamp or realignment as with conventional laser cutting systems. The fiber laser system is also more efficient and maintenance-free due to being air cooled, as opposed to water cooled, and operating on standard 110 volts AC power. Further, the fiber laser system may occupy as little as one-third the space occupied by conventional laser systems, thereby allowing for optimization of the square footage of manufacturing facilities.

The diode pumped fiber laser 40 incorporates a coaxial gas jet 50 and nozzle 51 that helps to remove debris from the kerf and cools the region where the beam interacts with the material as the beam cuts and vaporizes the metal. The coaxial gas jet nozzle (0.018 inch diameter (0.457 mm)) is centered around the focused beam with approximately 0.010 inch (2.54 mm) between the tip of the nozzle and the tubing 16. In many cases, the gas utilized in the jets may be reactive or non-reactive (inert). In the case of reactive gas, oxygen or compressed air may be used.

In one embodiment, the jet is pressurized with oxygen at 20 psi and is directed at the tube 16 with the focused laser beam 55 exiting the tip 53 of the nozzle (0.018 inch diameter (0.457 mm)). The oxygen reacts with the metal to assist in the cutting process very similar to oxyacetylene cutting. The focused laser beam acts as an ignition source and controls the reaction of the oxygen with the metal. In this manner, it is possible to cut the material with a very fine kerf with precision.

In other embodiments of the present invention, compressed air may be used in the gas jet 50 since it offers more control of the material removed and reduces the thermal effects of the material itself. Inert gas such as argon, helium, or nitrogen can be used to eliminate any oxidation of the cut material. The result is a cut edge with no oxidation, but there is usually a tail of molten material that collects along the exit side of the gas jet that must be mechanically or chemically removed after the cutting operation.

In either case, it is also necessary to block the laser beam 55 as it cuts through the top surface of the tube and prevent the beam, along with the molten metal and debris from the cut, from impinging on the inside opposite surface of the tube 16. To this end, a stainless steel mandrel 56 (approx. 0.034 inch diameter (0.864 mm)) is placed inside the tube and is allowed to roll on the bottom of the tube 16 as the pattern is cut. This acts as a beam/debris block protecting the far wall inner diameter.

Hence, the diode pumped fiber laser system 40 of the present invention enables the machining of narrow kerf widths while minimizing the heat input into the material. Thus, it is possible to make smooth, narrow cuts in the tube 16 in very fine geometries without damaging the narrow struts that make up the stent structure.

Cutting a fine structure also requires the ability to manipulate the tube with precision. The positioning of the tubular structure requires the use of precision CNC equipment such as that manufactured and sold by Anorad Corporation. In addition, a unique rotary mechanism has been provided that allows the computer program to be written as if the pattern were being cut from a flat sheet. This allows both circular and linear interpolation to be utilized in programming. Since the finished structure of the stent is very small, a precision drive mechanism is required that supports and drives both ends of the tubular structure as it is cut. Since both ends are driven, they must be aligned and precisely synchronized, otherwise the stent structure would twist and distort as it is being cut.

As discussed above, the cutting process utilizing the diode pumped fiber laser and gas jet cooling results in a very narrow kerf (approximately 0.0005 inch (0.0127 mm)) with the molten slag re-solidifying along the cut. This traps the cut-out scrap of the pattern requiring further processing. In order to remove the slag debris from the cut allowing the scrap to be removed from the remaining stent pattern, it is necessary to soak the cut tube 16 in a solution of HCl for approximately 8 minutes at a temperature of approximately 55° C. Before it is soaked, the tube is placed in a bath of alcohol/water solution and ultrasonically cleaned for approximately 1 minute to remove the loose debris left from the cutting operation. After soaking, the tube is then ultrasonically cleaned in the heated HCl for 1–4 minutes depending upon the wall thickness. To prevent cracking/breaking of the struts attached to the material left at the two ends of the stent pattern due to harmonic oscillations induced by the ultrasonic cleaner, a mandrel is placed down the center of the tube during the cleaning/scrap removal process. Upon completion of this process, the stent structures are rinsed in water. They are now ready for electropolishing.

The stents are preferably electrochemically polished in an acidic aqueous solution such as a solution of ELECTRO-GLO #300, sold by the ELECTRO-GLO Co., Inc. in Chicago, Ill., which is a mixture of sulfuric acid, carboxylic acids, phosphates, corrosion inhibitors, and a biodegradable surface active agent. The bath temperature is maintained at about 110–135° F. (43.33–57.2° C.) and the current density is about 0.4 to about 1.5 amps per in$^2$. Cathode to anode area should be at least about two to one. The stents may be further treated if desired, for example by applying a biocompatible coating. Other solutions and processes to electrochemically polish laser cut stents are known in the art.

Direct laser cutting produces edges which are essentially perpendicular to the axis of the laser cutting beam, in contrast with chemical etching and the like which produce pattern edges which are angled. Hence, the laser cutting process of the present invention essentially provides stent cross-sections, from cut-to-cut, which are square or rectangular, rather than trapezoidal; see FIG. 5a. The resulting stent structure provides superior performance.

It will be apparent from the foregoing that the present invention provides a new and improved method and apparatus for direct laser cutting of metal stents, enabling greater precision, reliability, structural integrity and overall quality, substantially without burrs, slag or other imperfections which might otherwise hamper stent integrity and performance. While the invention has been illustrated and described herein in terms of its use relative to an intravascular stent for use in arteries and veins, it will be apparent to those skilled in the art that the invention can be used to manufacture stents for other uses, such as the biliary tract, or to expand prostatic urethras in cases of prostate hyperplasia, and to manufacture other medical products requiring precision micro-machining.

Therefore, while particular forms of the invention have been illustrated and described, various modifications can be made without departing from the spirit and scope of the invention. Accordingly, it is not intended that the invention be limited, except as by the appended claims.

What is claimed:
1. A method of making a stent, comprising:
   providing a generally tubular member;
   providing a fiber laser comprised of:
      an optical fiber; and
      two or more mirrors;
   pumping said fiber laser using a diode pump; and
   cutting a predetermined pattern in the tubular member using the fiber laser.
2. The method of claim 1, further comprising gating the pump using a pulse generator.
3. The method of claim 2, further comprising locating the pulse generator external to the fiber laser.
4. The method of claim 2, further comprising pulsing the pulse generator at a frequency in the range of 100 to 3000 Hertz.
5. The method of claim 2, wherein the pulse generator provides laser pulses having pulse lengths between 0.05 and 0.50 milli-seconds.
6. The method of claim 1, wherein the fiber laser is air cooled.
7. The method of claim 2, wherein gating minimizes the heat affected zone of the tubular member during cutting.
8. The method of claim 1, wherein:
   the optical fiber has an active region between the mirrors; and
   the pump is external to and coaxial with the optical fiber.
9. The method of claim 1, wherein the mirrors allow wavelength transmission.
10. The method of claim 1, wherein the mirrors are parallel to one another.
11. The method of claim 1, wherein the fiber laser comprises:
   a first mirror; and
   a second mirror.
12. The method of claim 11, wherein the optical fiber has an active region between the first and second mirrors, and further comprising:
   passing a light having a wavelength through the first mirror;
   resonating the light in the active region;
   passing the light through the second mirror; and
   impinging the tubular member with the light.
13. The method of claim 1, further comprising controlling the operation of the fiber laser using computer numeric control.

* * * * *